(12) United States Patent
Hatfield et al.

(10) Patent No.: US 6,655,010 B1
(45) Date of Patent: Dec. 2, 2003

(54) METHOD FOR BATCH MANUFACTURING SENSOR UNITS

(75) Inventors: John Vernon Hatfield, Manchester (GB); David Grindrod, Market Drayton (GB); Paul James Travers, Chorlton (GB); Nicholas Neil Payne, Chorlton (GB)

(73) Assignee: Osmetech plc (GB)

( * ) Notice: Subject to any disclaimer, the term of this patent is extended or adjusted under 35 U.S.C. 154(b) by 200 days.

(21) Appl. No.: 09/662,675

(22) Filed: Sep. 15, 2000

Related U.S. Application Data

(63) Continuation of application No. PCT/GB99/00896, filed on Mar. 22, 1999.

(30) Foreign Application Priority Data

Mar. 20, 1998 (GB) ................................ 9805867

(51) Int. Cl.$^7$ ................... H01C 17/00; H01C 7/02; H05K 3/02; B23P 17/00
(52) U.S. Cl. ................... 29/610.1; 29/612; 29/846; 29/415
(58) Field of Search ............. 29/592, 592.1, 29/620, 621, 621.1, 612, 846, 830, 412, 413, 414, 415, 610.1; 174/257, 256, 261; 361/748, 765; 438/125

(56) References Cited

U.S. PATENT DOCUMENTS 5,828,133 A * 10/1998 Caillat et al. ............... 257/766
5,976,284 A * 11/1999 Calvert et al. ............... 156/51

FOREIGN PATENT DOCUMENTS

| EP | 0798772 | 1/1997 |
| EP | 0780890 | 6/1997 |
| EP | 0794428 | 9/1997 |
| WO | 9303355 | 2/1993 |
| WO | 9600383 | 1/1996 |
| WO | WO 96/00383 | * 1/1996 |

* cited by examiner

*Primary Examiner*—Carl J. Arbes
*Assistant Examiner*—Tim Phan
(74) *Attorney, Agent, or Firm*—Marger Johnson & McCollom, PC

(57) ABSTRACT

There is disclosed a method for manufacturing a batch of sensors including providing a substrate which has a plurality of conductive tracks formed thereon; electrochemically depositing a first active sensing material layer over the substrate and the conductive tracks in a process in which the conductive tracks are part of a single electrical circuit; removing deposited active sensing material from predetermined portions of the substrate: and sub-dividing the substrate to produce a plurality of sensor units.

14 Claims, 2 Drawing Sheets

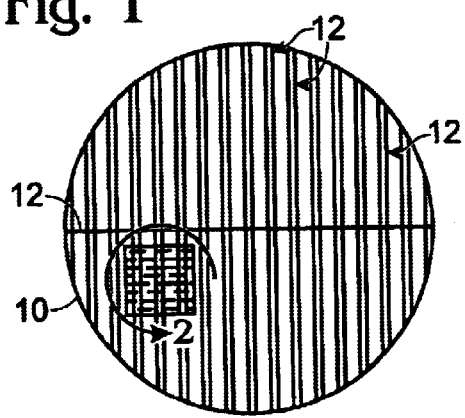
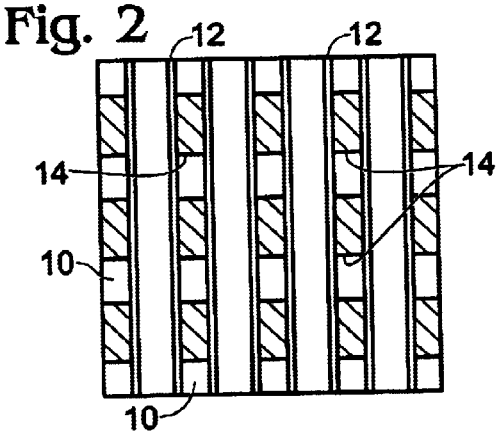
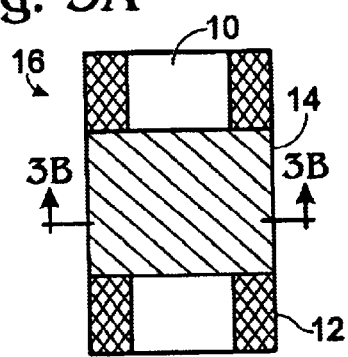
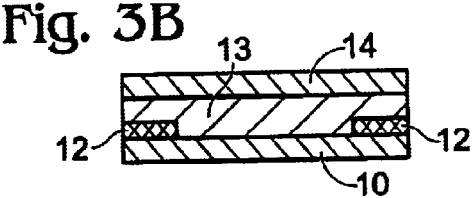
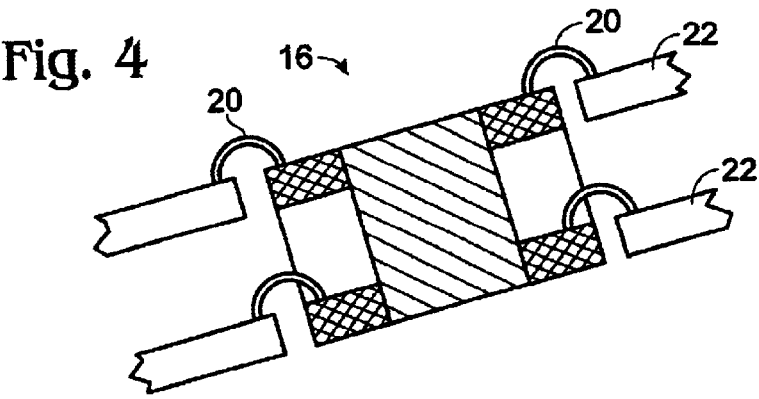

METHOD FOR BATCH MANUFACTURING SENSOR UNITS

This application is a continuation of International Application No. PCT/GB99/00896, filed Mar. 22, 1999.

BACKGROUND OF THE INVENTION

This invention relates to a method for manufacturing sensors, with particular, but by no means exclusive, reference to gas sensors comprising conducting polymers (CPs).

Gas sensors which employ conducting polymers (CPs), such as polypyrrole and substituted derivatives thereof, are well known (see for example, International Publications WO 96/00384, WO 96/00383, and K C Persaud and P Pelosi in "Sensors and Sensory Systems for an Electronic Nose", pp 237–256, eds J W Gardner and P N Bartlett, 1992, Kluwer Academic Publishers, Netherlands, and references therein). Typically, a single gas sensor is produced by depositing a layer of CP between a pair of electrodes, the sensor being operated as a chemiresistor, i.e. the presence of a gas is detected by measuring variations in the dc resistance of the CP, these variations being caused by adsorption of the gas onto the CP. It is also possible to detect ac impedance properties of the CP. It is common for a plurality of sensors to be incorporated into a single gas sensing device. Each sensor has a different CP and/or a different dopant anion, and thus each sensor displays different response characteristics. The use of such arrays of CP sensors allows gases, vapours and odours to be recognised by the response "fingerprint"—the pattern of sensor responses across the array. In this manner, an impressive range of gases can be detected and identified —either individually or as components of mixtures—with good sensitivity.

One problem associated with gas sensors of this kind is that of sensor to sensor reproducibility. Typically, the polymers are produced in their conducting state by electrochemical deposition of the polymer onto and between the electrodes. However, it is very difficult to standardise the deposition conditions, and hence the precise characteristics of the deposited CP, due to extraneous variations in parameters such as deposition voltage and current, monomer concentration, and dopant ion concentration. As a result; a batch of sensors of identical type which have had the same CP electrochemically deposited thereon, but at different times, may display variations in their response characteristics and basal resistances.

Gas sensor arrays of the type discussed can be monolithic, i.e. all of the gas sensors in the array are formed on a common substrate. Thus, another problem is that if a single sensor in the array malfunctions. It is not possible to replace the single sensor—the entire array must be replaced.

Another problem still is that the manufacture of gas sensing arrays using electrochemical deposition is a laborious process. Each array is manufactured separately and each sensor in the array comprises a different CP/dopant ion combination. Therefore, the production of x sensor arrays having y sensors in each array requires x,y separate electrochemical deposition processes.

SUMMARY OF THE INVENTION

The present invention overcomes the above mentioned-problems.

According to the invention there is provided a method for manufacturing a batch of sensors comprising the steps of:
providing a substrate which has a plurality of conductive tracks formed thereon;
electrochemically depositing an active sensing material over the substrate and the conductive tracks in a process in which the conductive tracks are part of a single electrical circuit;
removing deposited active sensing material from predetermined portions of the substrate; and sub-dividing the substrate to produce a plurality of sensor units.

In this way, electrochemical deposition conditions are identical for all of the eventually produced sensor units. Furthermore, a large number of sensors can be conveniently and efficiently produced in a few straightforward steps.

Preferably, the conductive tracks may be held at a common potential during the electrochemical deposition. One or more conductive tracks may be formed on the substrate so as to short circuit the other conductive tracks.

The sensors may be gas sensors.

The active sensing material may be conducting organic polymer (CP). Two or more layers of CP may be deposited on the substrate. The first layer of CP may be formed by a chemical oxidative process, and may be produced by a spin coating process.

The substrate may comprise silicon or ceramic.

The removal of deposited active sensing material may be performed by etching. Plasma etching or chemical etching may be used.

The substrate may be sub-divided by sawing or scribing the substrate to produce a plurality of sensor units.

A pattern corresponding to the position of the sensor units may be cut into the substrate prior to the sub-division of the substrate. The pattern may be cut before the step of electrochemically depositing the sensing material.

The pattern may be cut by sawing or scribing.

The substrate may be sub-divided by applying pressure to the substrate.

Heating elements for the sensor units may be incorporated into the substrate prior to the electrochemical deposition.

The batch may comprise at least one hundred sensor units, preferably at least three hundred, most preferably at least five hundred sensor units.

Methods in accordance with the invention will now be described with reference to the accompanying drawings, in which:

BRIEF DESCRIPTION OF THE DRAWINGS

FIG. 1 is a plan view of a substrate with conductive tracks formed thereon;

FIG. 2 is an enlarged view of the inset region of FIG. 1 marked "I" after conducting polymer has been removed from predetermined portions of the substrate;

FIG. 3A is a plan view of an individual sensor unit;

FIG. 3B is a cross-sectional side view of the sensor unit of FIG. 3A, taken along line 3*b*—3*b*;

FIG. 4 shows bond wire connection to a sensor unit;

DETAILED DESCRIPTION OF PREFERRED EMBODIMENT(S)

Figure 5:
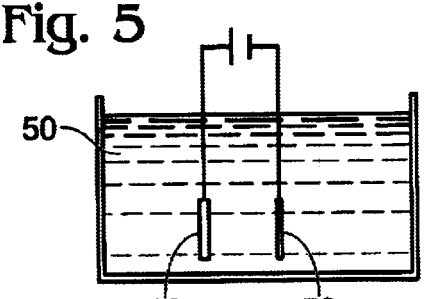
FIG. 5 shows an electrochemical deposition arrangement.

FIGS. 1–2 and 3A–3B depict-various stages in a method for manufacturing a batch of sensors comprising the steps of providing a substrate 10 which has a plurality of conductive tracks 12 formed thereon; depositing a first active sensing material 13 over the substrate 10 and the conductive tracks 12 in a process in which the conductive tracks are part of a single electrical circuit; depositing a second active sensing material layer 14 over the first layer 13; removing the deposited active sensing material from predetermined portion of the substrate 10; and sub-dividing the substrate 10 to produce a plurality of sensor units 16.

In this way, electrochemical deposition conditions are identical for all of the eventually produced sensor units. Furthermore, a large number of sensors can be conveniently and efficiently produced in a few straighfforward steps.

In one embodiment, the conductive tracks 12 are held at a common potential during the electrochemical deposition. A transverse conductive track 12a is formed on the substrate 10 so as to short circuit the other conductive tracks 12. The transverse track 12a spans the substrate 10 and is in electrical connection with the other conductive tracks 12. In this way, the conductive tracks 12 may be held at a uniform potential in order to ensure homogeneous electrochemical deposition conditions. Gold is a suitable material for the conductive tracks 12, although it will be apparent that other conductive materials might be employed, and that the conductive tracks may be short circuited in many other ways:— for example, an annular conductive track might be provided on the substrate which is in electrical contact with the other conductive tracks, or the conductive track might be short-circuited by the application of an external conductive arrangement to the substrate, such as a ring electrode formed from conductive material.

The sensor units 16 are gas sensors, although other forms of sensor produced by the general method are also within the scope of the invention.

The active sensing material is CP. In one method of manufacture, two or more layers of CP 13, 14 are deposited on the substrate 10, the first layer of CP 13 being formed by a chemical oxidative process, i.e. the polymer is produced in the conducting state by the action of a oxidising agent. Advantageously, a spin coating process is employed, in which the substrate is spin coated with a solution containing an oxddising agent such as ferric chloride, and the coated substrate is then exposed to monomer vapour.

Alternatively, a photopolymerisatlon process might be employed, in which the substrate is coated, preferably by spin coating, with a photosensitive solution containing the monomer. Polymerisation is effected by exposing the coated substrate to radiation of suitable wavelength (probably of UV wavelengths).

It will be apparent from the foregoing that the electrochemically deposited CP 14 is preferably deposited onto the first layer of CP 13, and therefore is not directly deposited over the substrate and the conductive tracks.

Polypyrrole is a suitable CP for use as a first, "base" layer 13, its use permitting the provision of relatively large spacings between adjacent conductive tracks (see International Publication No. WO 96/00383 for a discussion of this CP bilayer approach). However, the use of a single layer of electrochemically deposited CP is also within the scope of the invention, and, indeed, will generally be preferred when relatively narrow electrode spacings (less than about 25 μm) are employed. In this instance, the electrochemically deposited CP 14 can be deposited directly onto the substrate.

Having deposited a first layer of CP 13, a second layer of CP 14 is deposited electrochemically over the entire substrate surface, this second layer of CP 14 being in direct contact with the first layer 13 of CP. Methods for electropolymerisation CPs are well established in the art: see, for example, International Publication WO 86/01599; Persaud and Pelosi, ibid. The transverse conductive track 12a ensures that the conductive tracks 12 are held at a common potential during the electrodeposition and thus that the electrodeposition process is uniform over the entire substrate. FIG. 5 shows a simple electrochemical deposition in which the substrate 10 is immersed in a solution 50 containing appropriate concentrations of monomer and dopant counter-ion (the latter being incorporated into the charged, conductive polymer and ensuring overall electrical neutrality). The conductive tracks on the substrate 10 are appropriately connected so as to act as the anode of an electrical circuit. A plate cathode 52 is suspended in the solution 50 in proximity to the substrate 10. It is also possible to use a reference electrode, as is well-known in the art.

A preferred substrate material is silicon, which permits the use of planar processing technologies. However, other substrate materials, such as ceramics, are within the scope of the invention. It is likely that a silicon wafer will require light oxidation before the tracks and sensing material are deposited, since silicon itself is a semiconductor and would provide an alternative route for conduction. It is possible that intrinsic silicon would not require oxidation, owing to its high resistance. However, more commonly available n-type or p-type silicon would require light oxidisation.

The deposited CP is now removed from predetermined portions of the substrate in order to produce structures which correspond to individual sensor units. The removal process is by etching. Plasma etching is conveniently employed, although wet chemical etching is also possible. Suitable masks are employed to ensure that CP is removed according to the pattern shown in FIG. 2. The masks can be produced by photolithographic techniques. However, it should be noted that some CPs, can be deaoped by polar solvents and are thus not suited to the application of conventional thin film processing technologies. An alternative is to employ a "physical" mask, fabricated from a suitable material such as aluminium, and having a plurality of apertures corresponding to predetermined portions of the substrate from which CP is to be removed.

It should also be noted that it is possible to perform the step of removing CP after the substrate is subdivided, i.e. the removal is performed on a single sensor unit. It will be apparent, then, that the steps of removing deposited sensing material and sub-dividing the substrate can be performed in either order. However, it is preferred to remove the sensing material from the entire substrate because of the economy of scale.

The substrate is then subdivided to produce a plurality of sensor units 16. This sub-division may be by simply sawing the silicon wafer into the individual sensor units 16 it being noted that it is difficult to scribe oxidised silicon. A wafer saw is suitable for use with most CPs except those CPs which are sensitive to polar solvents, since wafer saws are usually water cooled. It may be possible to cool the blade with a non-polar solvent. Altematively, the CP may be protected by applying a removable protective layer, such as a photoresist, thereto. In a typical but non-limiting embodiment, a standard circular silicon wafer of 4" (10.2 cm) diameter is used to yield between 500 and 1600 identical sensor units of dimensions approx. 1 mm×2 mm. However, as described in the Examples below, smaller batches of 100–200 sensor units are possible. These sensor units can be handled with standard pick and place equipment. Larger silicon wafers of 5" (12.7 cm), 6" (15.2 cm) and 8" (20.3 cm) diameter are commercially available, and may be employed as substrates in the present invention.

It is also possible to pre[]scribe the substrate by cutting a pattern corresponding to the positions of the sensor units into the substrate (which remains whole) prior to the sub-division of the substrate. The pattern can be cut by scribing or sawing. It is preferred to partially saw through the wafer in the desired pattern from the underside of the substrate, i.e. the surface not supporting the tracks and sensing material. The pattern may be cut before the step of electrochemically deposition the sensing material—in this instance it is possible to use a water cooled wafer saw before deposition polar solvent sensitive CPs. The substrate can be sub-divided by applying pressure to the substrate, such as by rolling a roller over the underside of the substrate with a slight pressure.

The sensor units can be mounted on a ceramic carrier. A channel can be provided in the carrier in which the sensor units can reside. The channel can be formed by laser ablation of the carrier. FIG. 4 depicts a sensor unit 16 in which the conductive track 12 is connected by bond wires 20 to appropriate conductive rails 22. The conductive rails 22 are ultimately connected to suitable sensor interrogation means, which might apply direct or alternating current to the sensor unit. Alternatively, adhesive bonding is possible—preferably using a material, such as silver loaded polyamide, which does not outgas greatly.

The invention also provides sensor arrays comprising a plurality of different gas sensors. The sensors in the array can be mounted on a ceramic carrier in the manner described above. Clearly, if an array having y different sensors is desired, then y separate electropolymerisations are required. However, using the method of the present invention, these y electropolymerisatlons can yield over five hundred identical gas sensors. Therefore, over five hundred arrays can be produced which exhibit highly standardised responses. Another advantage is that these are easily and economically repaired by directly replacing any damaged sensors.

It is well known in the art that it is difficult to bridge electrodes with CP when the separation of the electrodes exceeds the length of the polymeric chains. In practical terms, this means that many CPs cannot span electrode gaps of greater than 25 $\mu$m, and very few can span electrode gaps of greater than 100 $\mu$m, at least not without undesirable consequences such as dramatic increases in polymer resistance. However, it is desirable to span larger electrode gaps, certainly if the CP is used as the active component of a gas sensor, because inter alia higher thresholds for saturation of the response of the sensor are achieved. One way of overcoming this problem is to electrochemically deposit CP onto a first layer of a suitable CP, as described previously. Another solution is to electrochemically deposit a second layer of CP across a series of electrodes having ensured that the separation of adjacent pairs of electrodes in the series is sufficiently small that the deposited a second layer of CP can successfully bridge each adjacent pair of electrodes. A gas sensor of the type described above can be produced by subsequently making appropriate electrical connection to a single, well separated, pair of electrodes. Usually, of course, this pair of electrodes would comprise the first and last electrodes in the series. In this instance, a sensor is produced in which the gap between the "active" electrodes, connected for gas sensing purposes, is very large, even though the gap between the electrode used for electrochemical depositing is small.

Figure 7:
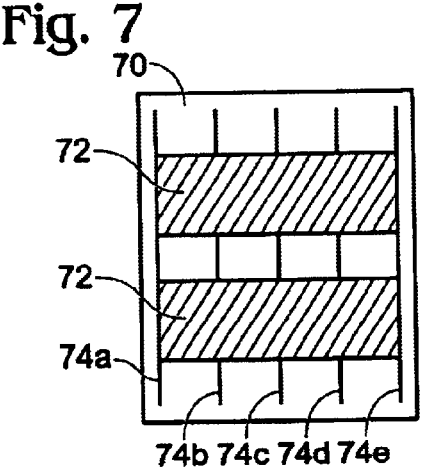
FIG. 7 is a view of a region of a substrate after-conducting polymer has been selectively removed therefrom so as to span a number of conductive tracks.
Figure 8:
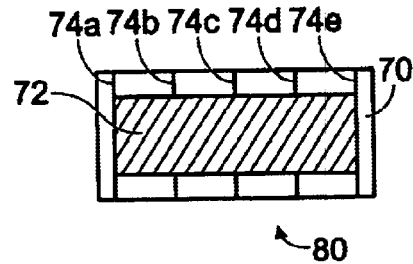
FIG. 8 shows a sensor uni produced by sub-division of the region shown in FIG. 7.

Sensor units of this type may be readily produced according to the present invention by appropriate removal of CP from the substrate. FIG. 7 shows a portion of a substrate 70 after CP is removed from predetermined portion of the substrate so that the remaining CP is present as strips 72, each strip 72 bridging five successive conductive tracks 74a–e, 76a–e. FIG. 8 shows a sensor unit 80 produced after appropriate sub-division of the substrate 70. Electrical connection to the sensor unit 80 is made via conductive tracks 74a, 74e. The remaining conductive tracks 74b, c, and d might be etched so as not to protrude from underneath the CP strip 72. The precise number of electrodes associated with such strip, their width and their mutual separation would be selected depending on the CP to be deposited.

Some specific Examples which utilise the principles set out above will now be described.

EXAMPLE 1

Figure 6:
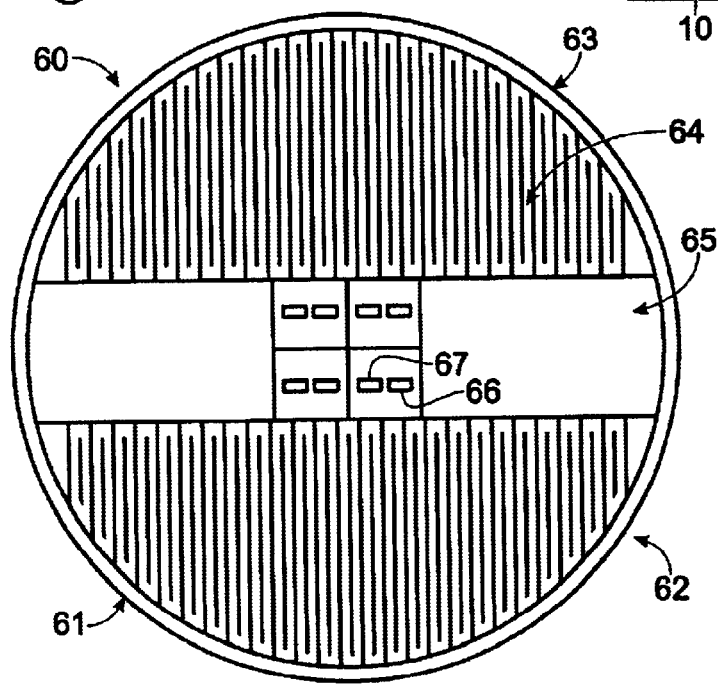
FIG. 6 shows a patterned silicon wafer.

3" silicon wafers are prepared by sequentially depositing SiO$_2$ (approx. 1 $\mu$m thickness) and chromium (approx. 50 nm thickness). Gold (approx. 500 nm thickness) is deposited onto the silicon wafer and this gold layer is subsequentlally patterned to produce a patterned wafer substantially as shown in FIG. 6. The patterned wafer comprises four sections, shown generally at 60, 61, 62, 63. Each section comprises gold tracks 64 with a common connecting track 65, and two isolated gold pads 66, 67. The gold pads 66, 67 are useful for resistance measurements of CP subsequently deposited therebetween. An annular gold track 68 is also situated on the wafer.

The patterned wafer is then spin coated with approx. 3.5 M FeCl$_3$ solution (in 1-methoxypropanol), and polypyrrole deposited thereon from pyrrole vapour. Next, a photoreslst is applied, by spin coating on HPR507 (120° C. for 30 minutes). The wafer is then sawn into four 19×30 mm pieces, each piece corresponding to a different section 60, 61, 62, 63. The photoresist protects the polypyrrole from water, which is used as a coolant during sawing. The photoresist is then removed from each piece in an acetone wash.

A second layer of CP is deposited electrochemically onto each 19×30 mm piece using methods well established in the art, electrical connection to the gold tracks 64 being made via the connecting track 65. It has been found that, by sub-dividing the wafer into four pieces, a trade-off is reached between ease of electrodeposition and the amount of monomer solution required verses the number of sensors eventually realised from each electrodeposition. After electrodeposition, the pieces are subjected to a heat treatment step (200° C.) for varying periods, in which the resistance of the CP between the pads 66, 67 is monitored until a desired resistance value is attained.

A photoresist is then applied to each piece using the method described above. Next aluminium is evaporated onto the pieces and another layer of positive photoresist applied (S1813, 80° C./30 min). Substrates are patterned, then etched (80% phosphoric acid, 10% acetic acid, 5% nitric acid, 5% water) so that "pads" of aluminium bridge the gold tracks. The aluminium is removed, and a further photoresist is applied to protect the CPs before each piece is sawn to provide a plurality of individual sensor units (approx. 1×2 mm). The sensor units are glued (PROTOVIC 1 361 SC) onto a ceramic substrate, the glue being cured at 76° C. for 90 minutes. Pick and place equipment is used to position the sensors. Wires are bonded to the ceramic substrate, and appropriate resistance checks are made.

Instead of selectively removing CP by depositing aluminium and etching to produce a mask, each piece can be placed against a permanent, "physical" aluminium mask and then plasma etched. A photoresist is then applied to each piece which is sawed to produce individual sensor units.

EXAMPLE 2

A patterned wafer, substantially as shown in FIG. 6, is produced using the methods described in Example 1. The wafer is pre-scribed on its reverse face into 1×2 mm units, and then a polypyrrole base layer is deposited as set out in Example 1. The wafer is then snapped to provide four 19×30 mm pieces. Electrochemical deposition of a second CP layer onto each piece is accomplished as set out in Example 1. Removal of CP from selected areas of each piece can be accomplished using the approaches described in Example 1, or this step can be accomplished manually using a scalpel. Each piece is then snapped into 1×2 mm individual sensor units which can be disposed on a substrate as previously described.

EXAMPLE 3

The method described in Example 2 is used to provide pieces having a polypyrrole base layer and a CP second layer, except that the silicon wafer is pre-scribed into four 19×30 mm sections rather than 1×2 mm sections. After heat treatment of the second layer of CP, removal of CP from selected areas of each piece can be accomplished using the approaches described in Example 1. Alternatively, a photoresist can be spin coated to each piece (HPR 507, 120° C. for 30 minutes) and the piece sawn to provide individual sensor units (approx. 1×2 mm). The sensor units are glued to the substrate as described in Example 1 and the photoresist is removed. CP is then selectively removed using a scalpel. Wire bonding and resistance checking steps are then performed as described in Example 1.

It should be noted that the methods described in Examples 1 to 3 can also be applied to the deposition of CP onto ceramic wafers.

Heating elements for the sensor units can be incorporated into the substrate prior to the electrochemical deposition. For example, with a silicon substrate, a heating resistor can be integrated on the site of each sensor unit from a high resistance polysilicon layer. Alternatively, a diffused resistor or a platinum heating element might be used. The incorporation of a heating element permits individual temperature control of the sensor units. A temperature sensing element such as a diode could also be fabricated onto the site of each sensor unit before the electrochemical deposition step, although it should be noted that a platinum heating element could be used as a resistance thermometer. The likely order of such a manufacturing process would be fabrication of the diode; followed by provision of the heating resistor; followed by deposition of gold conductive tracks; followed by CP deposition. Additionally bond pads (probably in aluminium) would be required for the diode and the resistor. Other "active" circuitry, such as amplifier gain stages, could be incorporated into a silicon substrate.

What is claimed is:

1. A method for batch manufacturing sensor units, comprising:

providing a substrate which has a plurality of conductive tracks formed thereon as part of a single electrical circuit;

forming a first conducting polymer layer on the substrate;

electrochemically depositing a second conducting polymer layer over the first conducting polymer layer to produce a substrate area in which the substrate and conductive tracks are completely overlaid with the first conducting polymer and the second conducting polymer;

removing the deposited conducting polymers from predetermined portions of the substrate area; and sub-dividing the substrate area to produce a plurality of sensor units.

2. A method according to claim 1 in which the conductive tracks are held at a common potential during the electrochemical deposition of the second conducting polymer layer.

3. A method according to claim 2 in which one or more of the conductive tracks is formed on the substrate so as to short circuit the other conductive tracks.

4. A method according to claim 1 in which the first conducting polymer layer is formed by a chemical oxidative process.

5. A method according to claim 1 in which the substrate comprises silicon.

6. A method according to claim 1 in which the substrate is ceramic.

7. A method according to claim 1 in which the removal of deposited active sensing material is performed by etching.

8. A method according to claim 7 in which plasma etching is used.

9. A method according to claim 1 in which a pattern corresponding to the positions of the sensor units is cut into the substrate prior to the subdivision of the substrate.

10. A method according to claim 9 in which the pattern is cut before the step of depositing the first active sensing material layer.

11. A method according to claim 9 in which the pattern is cut by sawing or scribing.

12. A method according to claim 9 in which the substrate is subdivided by applying pressure to the substrate.

13. A method according to claim 1 in which the plurality comprises at least one hundred sensor units.

14. A method according to claim 1 in which the plurality comprises at least three hundred sensor units.

* * * * *

UNITED STATES PATENT AND TRADEMARK OFFICE
CERTIFICATE OF CORRECTION

PATENT NO.    : 6,655,010 B1
DATED         : December 2, 2003
INVENTOR(S)   : Hatfield et al.

It is certified that error appears in the above-identified patent and that said Letters Patent is hereby corrected as shown below:

Title page, Item [54] and Column 1, line 2,
Title, "METHOD FOR BATCH MANUFACTURING SENSOR UNITS" should read -- A METHOD FOR BATCH MANUFACTURING SENSOR UNITS --.

Title page,
Item [56], References Cited, FOREIGN PATENT DOCUMENTS,
"EP     0798772     1/1997" should read -- EP     0798772     10/1997 --.

Column 1,
Line 13, "known (see for example," should read -- known (see, for example, --.
Line 42, "a result; a" should read -- a result, a --.
Line 50, "malfunctions. It" should read -- malfunctions, it --.
Line 58, "requires x,y separate" should read -- requires x.y separate --.
Line 62, "mentioned-problems" should read -- mentioned problems --.

Column 2,
Line 58, "after-conducting" should read -- after conducting --.
Line 61, "sensor uni produced" should read -- sensor unit produced --.
Line 66, "depict-various" should read -- depict various --.

Column 3,
Line 13, "few straighfforward steps." should read -- few straightforward steps. --.
Line 42, "an oxddising agent" should read -- an oxidizing agent --.
Line 44, "a photopolymerisatlon process" should read -- a photopolymerisation process --.
Line 53, "not directly deposited" should read -- not directly deposited --.

Column 4,
Line 37, "be deaoped by" should read -- be de-aoped by --.
Line 45, "is subdivided," should read -- is sub-divided, --.
Line 52, "then subdivided to" should read -- then sub-divided to --.
Line 59, "solvent. Alternatively, the" should read -- solvent. Alternatively, the --.

Column 5,
Line 4, "to pre[]scribe the" should read -- to pre-scribe the --.
Line 24, "unit.Alternatively, adhesive" should read -- unit. Alternatively, adhesive --.
Line 34, "y electropolymerisatlons can" should read -- y electropolymerisations can --.

UNITED STATES PATENT AND TRADEMARK OFFICE
CERTIFICATE OF CORRECTION

PATENT NO. : 6,655,010 B1
DATED : December 2, 2003
INVENTOR(S) : Hatfield et al.

It is certified that error appears in the above-identified patent and that said Letters Patent is hereby corrected as shown below:

Column 6,
Line 20, "is subsequentlally patterned" should read -- is subsequentially patterned --.
Line 31, "a photoreslst is" should read -- a photoresist is --.
Line 54, "pieces and another" should read -- pieces, and another --.

Column 7,
Line 51, "would be fabrication" should read -- would be: fabrication --.

Signed and Sealed this

Twentieth Day of July, 2004

JON W. DUDAS
*Acting Director of the United States Patent and Trademark Office*